United States Patent
Sarver, Jr. et al.

(10) Patent No.: US 9,850,457 B2
(45) Date of Patent: Dec. 26, 2017

(54) MICROBIAL GROWTH DETECTOR

(75) Inventors: Ronald Waldo Sarver, Jr., Dexter, MI (US); Alexandr Y. Kariagin, East Lansing, MI (US); Christine Claire Cooper, Williamston, MI (US); Susan Teruko McDougal, Novi, MI (US)

(73) Assignee: NEOGEN CORPORATION, Lansing, MI (US)

(*) Notice: Subject to any disclaimer, the term of this patent is extended or adjusted under 35 U.S.C. 154(b) by 402 days.

(21) Appl. No.: 12/928,960

(22) Filed: Dec. 23, 2010

(65) Prior Publication Data

US 2011/0275112 A1    Nov. 10, 2011

Related U.S. Application Data

(60) Provisional application No. 61/343,892, filed on May 5, 2010.

(51) Int. Cl.
  *C12Q 1/04* (2006.01)
  *B05D 3/02* (2006.01)
  (Continued)

(52) U.S. Cl.
  CPC ............ *C12M 23/22* (2013.01); *C12M 23/24* (2013.01); *C12M 41/26* (2013.01); *C12M 41/34* (2013.01);
  (Continued)

(58) Field of Classification Search
  CPC ...... C12M 23/22; C12M 23/24; C12M 42/26; C12M 41/34; G01N 31/22; G01N 33/02; G01N 21/80
  (Continued)

(56) References Cited

U.S. PATENT DOCUMENTS 4,868,110 A * 9/1989 DesRosier et al. ............ 435/34
4,945,060 A 7/1990 Turner et al.
(Continued)

FOREIGN PATENT DOCUMENTS

WO  WO 2009/091402 A1  7/2009

OTHER PUBLICATIONS

Form PCT/IB/326 Notification Concerning Transmittal of Copy of International Preliminary Report on Patentability (Chapter 1 of the Patent Cooperation Treaty), dated Nov. 15, 2012.
(Continued)

*Primary Examiner* — William H Beisner
*Assistant Examiner* — Danielle Henkel
(74) *Attorney, Agent, or Firm* — Honigman Miller Schwartz and Cohn LLP; Douglas H. Siegel; Jonathan P. O'Brien

(57) ABSTRACT

The disclosure generally relates to a test device that detects microorganism growth by detecting a gas metabolite (e.g., carbon dioxide) produced during the growth of bacteria or other microorganism in a tested sample. The test device can contain a culture growth media separated from a detection area by a gas-permeable membrane. The gas-permeable membrane permits carbon dioxide to permeate into the detection area. The detection area includes a solidified mixture of pH indicators and a gelling agent in the form of a semi-permeable matrix. The optical properties, including the absorbance of light at various wavelengths, of the detection solution change with alterations in carbon dioxide concentration. This test device can then be placed in an incubation and optical detection instrument to monitor changes in optical properties of the detection are induced during microorganism growth in the culture medium.

38 Claims, 5 Drawing Sheets

(51) Int. Cl.
*C12M 1/34* (2006.01)
*C12M 1/00* (2006.01)
*C12M 1/04* (2006.01)
*G01N 31/22* (2006.01)
*G01N 33/02* (2006.01)
*G01N 21/80* (2006.01)

(52) U.S. Cl.
CPC ............ *G01N 31/22* (2013.01); *G01N 33/02* (2013.01); *G01N 21/80* (2013.01)

(58) Field of Classification Search
USPC .............. 435/29, 287.2, 34, 287.5; 427/2.11
See application file for complete search history.

(56) References Cited

U.S. PATENT DOCUMENTS

| | | | |
|---|---|---|---|
| 5,094,955 A | | 3/1992 | Calandra et al. |
| 5,162,229 A | | 11/1992 | Thorpe et al. |
| 5,164,796 A | * | 11/1992 | Di Guiseppi et al. ........ 356/445 |
| 5,217,876 A | | 6/1993 | Turner et al. |
| 5,366,873 A | | 11/1994 | Eden et al. |
| 5,408,999 A | * | 4/1995 | Singh .................. G01N 21/643 436/136 |
| 6,153,400 A | | 11/2000 | Matsumura et al. |
| 6,197,576 B1 | | 3/2001 | Eden |
| 6,395,537 B1 | | 5/2002 | Eden et al. |
| 7,071,005 B1 | | 7/2006 | Eden |
| 2001/0039033 A1 | | 11/2001 | Ogawa |
| 2002/0127630 A1 | * | 9/2002 | DiGuiseppi et al. ........... 435/34 |
| 2004/0265440 A1 | | 12/2004 | Morris et al. |
| 2005/0266516 A1 | | 12/2005 | Kanipayor et al. |
| 2007/0015977 A1 | * | 1/2007 | McCann et al. .............. 600/309 |
| 2008/0113404 A1 | | 5/2008 | Eden et al. |
| 2008/0176273 A1 | | 7/2008 | Eden et al. |
| 2009/0032734 A1 | * | 2/2009 | Eden .......................... 250/459.1 |
| 2010/0273209 A1 | | 10/2010 | Eden et al. |

OTHER PUBLICATIONS

International Search Report and the Written Opinion of the International Searching Authority dated Dec. 23, 2010, for Application No. PCT/US10/03242.

Borisov, Sergey M., "Optical Carbon Dioxide Sensors Based on Silicone-Encapsulated Room-Temperature Ionic Liquids," Chem. Mater. 2007, 19, 6187-6194.

* cited by examiner

MICROBIAL GROWTH DETECTOR

CROSS-REFERENCE TO RELATED APPLICATION

Priority is claimed to U.S. Provisional Application No. 61/343,892, filed May 5, 2010, the disclosure of which is incorporated herein in its entirety.

BACKGROUND OF THE DISCLOSURE

Field of the Disclosure

Detection of bacterial (or other microorganism) contamination in food, drink, and food processing equipment is required to ensure a safe food supply. Detection methods are needed that detect multiple strains of bacteria at levels that, if left unchecked, would lead to food contamination. Described herein is a rapid, easy to use method, to detect total viable bacterial counts in samples related to the food industry, consumer products, nutraceutical products, environmental samples, and other sample types/matrices.

Related publications directed to methods and apparatus for detecting microorganisms (e.g., in a liquid medium) based on a signal such as pH change, carbon dioxide change, colorimetric change, or fluorimetric change include U.S. Pat. Nos. 4,945,060; 5,094,955; 5,162,229; 5,164,796; 5,217,876; 5,366,873; 6,197,576; 2008/0113404; 2008/0176273, and 2009/0032734. U.S. Pat. No. 6,153,400 is directed to a method and device for microbial antibiotic susceptibility testing. U.S. Pat. No. 7,071,005 is directed to a method and device for concentrating microorganisms. U.S. Publication No. 2005/0266516 is directed to a system for rapid analysis of microbiological materials in liquid samples. Borisov et al. (*Chem. Matr.*, vol. 19, p. 6187-6194 (2007)) is directed to optical carbon dioxide sensors based on silicon-encapsulated room-temperature ionic liquids.

The present disclosure relates to a test device used for the rapid detection of carbon dioxide or other metabolic gases resulting from microorganism growth in a culture medium that contains a sample (a sample in the food supply chain) to be tested for the presence of bacteria or other microorganisms.

SUMMARY

Described herein is a test device used for the rapid detection of bacterial and other microorganism growth in a culture medium. Detection of aerobic microorganism growth is based on detection of carbon dioxide ($CO_2$) produced during microorganism growth. The test device includes indicator molecules held in a container with optically transparent windows that are separated from a liquid media by a membrane through which carbon dioxide can permeate. The indicator molecules provide rapid detection of carbon dioxide by changing optical properties in the presence of carbon dioxide that is released during bacterial growth. The test device can be placed in an optical detection instrument which passes light through the test device to monitor changes in optical properties of the indicator/sensor molecules. The pH of the indicator molecules is adjusted for optimal response to carbon dioxide concentration. The indicator molecules may be contained in an agar matrix and sealed with a carbon dioxide permeable layer of silicone. Various growth media and platforms may also be overlaid in the test device which can also be sealed.

The disclosure relates to an apparatus for detecting carbon dioxide, the apparatus comprising: (a) a vessel comprising a wall, the wall defining (i) a detection region in the vessel and (ii) a growth region in the vessel; (b) a semi-permeable matrix disposed in the detection region of the vessel, the matrix comprising a pH indicator distributed throughout the matrix; (c) a gas-permeable membrane disposed inside the vessel, the gas-permeable membrane defining a boundary between the detection region and the growth region of the vessel; (d) optionally, a culture medium (e.g., tryptic soy broth) disposed in the growth region on the vessel, the culture medium being capable of supporting the growth of a microorganism and (e) optionally, a support material disposed in the growth region of the vessel, the support material providing a growth substrate for the microorganism; wherein: (i) the gas-permeable membrane and the semi-permeable matrix are permeable to carbon dioxide, thereby permitting diffusive transport of carbon dioxide present in the growth region to the detection region; (ii) the gas-permeable membrane is impermeable to liquid and solid materials present in the growth region; (iii) optionally, the gas-permeable membrane is substantially free of any pH indicators present in the semi-permeable matrix; and (iv) the wall of the vessel is at least partially transparent in the detection region.

The disclosure relates more generally to an apparatus for detecting a metabolic product gas of a microorganism, the apparatus comprising: (a) a vessel comprising a wall, the wall defining (i) a detection region in the vessel and (ii) a growth region in the vessel; (b) a semi-permeable matrix disposed in the detection region of the vessel, the matrix comprising a gas indicator distributed throughout the matrix; (c) a gas-permeable membrane disposed inside the vessel, the gas-permeable membrane defining a boundary between the detection region and the growth region of the vessel; and (d) optionally, a culture medium disposed in the growth region on the vessel, the culture medium being capable of supporting the growth of a microorganism; wherein: (i) the gas-permeable membrane and the semi-permeable matrix are permeable to a metabolic product gas of microorganism growth (e.g., $CO_2$, $N_2$, $H_2$, $O_2$, and/or others), thereby permitting diffusive transport of the gas(es) present in the growth region to the detection region; (ii) the gas-permeable membrane is impermeable to liquid and solid materials present in the growth region; (iii) optionally, the gas-permeable membrane is free or substantially free of any gas indicators present in the semi-permeable matrix; and (iv) the wall of the vessel is at least partially transparent in the detection region.

Various embodiments of the disclosed apparatus are possible. For example, the gas-permeable membrane can comprise a silicone polymer such as room-temperature-vulcanized silicone, high-temperature-vulcanized silicone, and/or ultraviolet-vulcanized silicone. The gas-permeable membrane is suitably attached to the wall of the vessel and forms a barrier isolating the detection region from the growth region. The gas-permeable membrane can have a thickness ranging from 10 µm to 2000 µm and/or can have permeability ranging from $1 \times 10^{-11}$ cm$^2$/(sec·Pa) to $1 \times 10^{-9}$ cm$^2$/(sec·Pa) for carbon dioxide. The semi-permeable matrix can be in the form of a solid, semi-solid, or gel, for example a gel comprising a gelling agent selected from the group consisting of agar, gelatin, carageenan, pectin, and combinations thereof. The semi-permeable matrix also can be adhered to the wall of the vessel. The pH indicator can exhibit a color change at a pH value ranging from 6 to 10, with suitable indicators being selected from the group consisting of bromothymol blue, xylenol blue, methyl orange, α-naphtholphthalein, fluorescein, coumarin, phenolphthalein, thymolphthalein, thymol blue, xylenol blue, and α-naphtholbenzein, and combinations thereof. In an embodiment, (i) the pH indicator comprises a first indicator and a second indicator; and (ii) semi-permeable matrix comprises the first indicator and the second indicator in amounts and at a pH such that (A) the semi-permeable matrix has a first absorbance at a first wavelength, (B) the semi-permeable matrix has a second absorbance at a second wavelength, and (C) a ratio of the first absorbance to the second absorbance ranges from 0.2 to 4. In a refinement, (i) the pH indicator comprises bromothymol blue and xylenol blue; and (ii) semi-permeable matrix comprises the bromothymol blue and the xylenol blue in amounts and at a pH such that (A) the semi-permeable matrix has a first absorbance at a first wavelength of about 615 nm, (B) the semi-permeable matrix has a second absorbance at a second wavelength of about 420 nm, and (C) a ratio of the first absorbance to the second absorbance ranges from 0.8 to 2.0. The growth region of the vessel, and the culture medium, when present, can be free of any pH indicators present in the semi-permeable matrix.

The disclosure also relates to a method (continuous or batch) of making an apparatus for detecting carbon dioxide according to any of the various disclosed embodiments, the method comprising: (a) providing a vessel comprising a wall, the wall defining (i) a detection region in the vessel and (ii) a growth region in the vessel, wherein the detection region of the vessel contains a semi-permeable matrix disposed in the detection region of the vessel, the matrix comprising a pH (or gas) indicator distributed throughout the matrix; (b) applying a gas-permeable membrane precursor in liquid form to an exposed surface of the semi-permeable matrix; and (c) curing the gas-permeable membrane precursor, thereby forming a gas-permeable membrane in the vessel, the gas-permeable membrane defining an interface between the detection region and the growth region of the vessel; wherein: (i) the gas-permeable membrane and the semi-permeable matrix are permeable to carbon dioxide, thereby permitting diffusive transport of carbon dioxide (or other target gases) present in the growth region to the detection region; (ii) the gas-permeable membrane is impermeable to liquid and solid materials present in the growth region; and (iii) the wall of the vessel is at least partially transparent in the detection region. The semi-permeable matrix in part (a) can be formed by a process comprising: (i) providing a mixture comprising (A) a liquid medium, (B) a matrix-forming agent in the liquid medium, and (C) a pH indicator in the liquid medium, wherein the mixture is at a temperature sufficient to maintain the mixture in liquid form; (ii) dispensing the mixture in liquid form into the detection region; (iii) cooling the mixture for a time sufficient to allow the matrix-forming agent to solidify, thereby forming the semi-permeable matrix comprising the pH indicator distributed throughout the matrix. In an extension, the method further comprises: (d) dispensing a culture medium in liquid form into the growth region of the vessel, the culture medium being in contact with the gas-permeable membrane and being capable of supporting the growth of a microorganism; (e) sealing the vessel; and (f) optionally exposing the sealed vessel to an ambient source of environmental carbon dioxide for a time sufficient for the semi-permeable matrix to attain an equilibrium level of carbon dioxide. In another refinement, part (d) of the method further comprises inserting a support material into the growth region of the vessel, the support material being in contact with the culture medium and providing a growth substrate for the microorganism.

Various embodiments of the disclosed methods are possible. For example, the mixture can be a solution in which the matrix-forming agent (e.g., agar, gelatin, carageenan, and/or pectin) and the pH indicator are dissolved in the liquid medium. The gas-permeable membrane precursor can be applied in an amount sufficient to completely coat the exposed surface of the semi-permeable matrix and to contact the wall of the vessel, for example to form a semi-permeable matrix adhered to the wall of the vessel. Curing the gas-permeable membrane precursor (e.g., a mixture comprising (i) a silicone prepolymer, (ii) a silicone crosslinking agent, and (iii) a curing catalyst) suitably comprises exposing the gas-permeable membrane precursor to ultraviolet light.

The disclosure also relates to a method of detecting carbon dioxide (or other metabolic product gas of a microorganism), the method comprising: (a) providing the apparatus for detecting carbon dioxide (or other metabolic product gas) according to any of the various disclosed embodiments including the culture medium disposed in the growth region on the vessel; (b) inserting a sample to be tested into the culture medium at a first time ($t_1$); (c) optionally, sealing the vessel with the inserted sample; (d) monitoring the detection region at a second time ($t_2 > t_1$) to detect changes in color of the pH (or gas) indicator in the semi-permeable matrix; (e) correlating a change in the color of the pH (or gas) indicator between the first time and the second time with a presence of carbon dioxide (or other metabolic product gas) in the detection region; and optionally (f) correlating a change in the color of the pH (or gas) indicator between the first time and the second time with a presence of microorganisms (e.g., bacteria such as aerobic bacteria producing carbon dioxide or other gas as a metabolite, yeasts, molds) in the sample.

Various embodiments of the disclosed methods are possible. For example, monitoring the detection region can comprise incubating the vessel at a controlled temperature between the first time and the second time. Monitoring the detection region can comprise visually inspecting the semi-permeable matrix in the detection region to detect the changes in color of the pH indicator. Alternatively or additionally, monitoring the detection region can comprise performing a spectrophotometric detection at one or more wavelengths (e.g., in the visible spectrum).

All patents, patent applications, government publications, government regulations, and literature references cited in this specification are hereby incorporated herein by reference in their entirety. In case of conflict, the present description, including definitions, will control.

Additional features of the disclosure may become apparent to those skilled in the art from a review of the following detailed description, taken in conjunction with the examples, drawings, and appended claims, with the understanding that the disclosure is intended to be illustrative, and is not intended to limit the claims to the specific embodiments described and illustrated herein.

BRIEF DESCRIPTION OF THE DRAWINGS

For a more complete understanding of the disclosure, reference should be made to the following detailed description and accompanying drawing wherein:

FIG. 2A is a side cross-section and FIG. 2B is a lateral/radial cross section along line A-A' of FIG. 2A.

FIG. 5A is a front view and FIG. 5B is a side cross section along line A-A' of FIG. 5A.

Figure 1A:
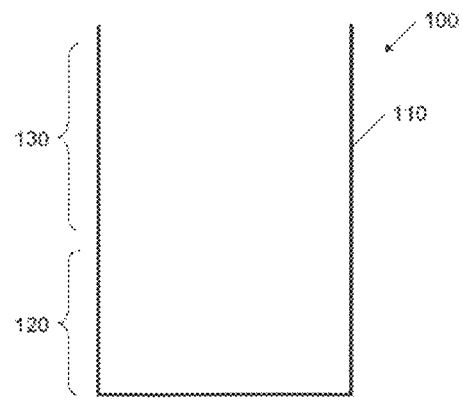
FIGS. 1A-1E illustrate side cross-sections of a detection apparatus and a method for making the same according to the disclosure.

While the disclosed apparatus and methods are susceptible of embodiments in various forms, specific embodiments of the disclosure are illustrated in the drawings (and will hereafter be described) with the understanding that the disclosure is intended to be illustrative, and is not intended to limit the claims to the specific embodiments described and illustrated herein.

DETAILED DESCRIPTION

The present disclosure generally relates to a test device that detects microorganism growth by detecting a gas metabolite (e.g., carbon dioxide) produced during the growth of bacteria or other microorganism in a tested sample. The test device can be a cylindrical chamber containing a bacterial growth media (e.g., tryptic soy broth (TSB)) separated from a detection area by a gas-permeable membrane. The gas-permeable membrane can be a silicone such as poly(dimethylsiloxane) that permits carbon dioxide to permeate into the detection area. The detection solution includes a mixture of pH indicators (e.g., bromothymol blue and xylenol blue) and a gelling agent (e.g., agar) to form a semi-permeable matrix. The optical properties of the detection solution are suitably adjusted so the absorbance ratio of light at 615 nm and 420 nm is near 1.0. The optical properties, including the absorbance of light a various wavelengths, of the detection solution changes with alterations in carbon dioxide concentration. In an embodiment, the detection solution is held in a chamber with optically transparent windows. This test device can then be placed in an optical detection instrument to monitor changes in optical properties during bacterial growth.

Detection Apparatus

Figure 1B:
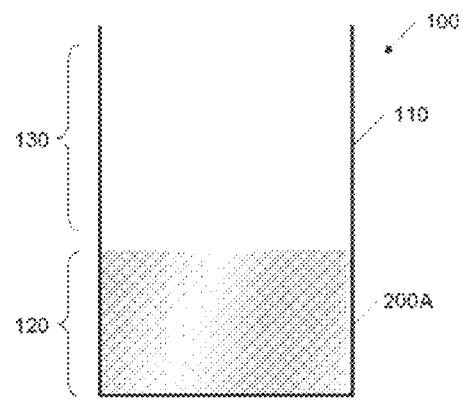
Figure 1C:
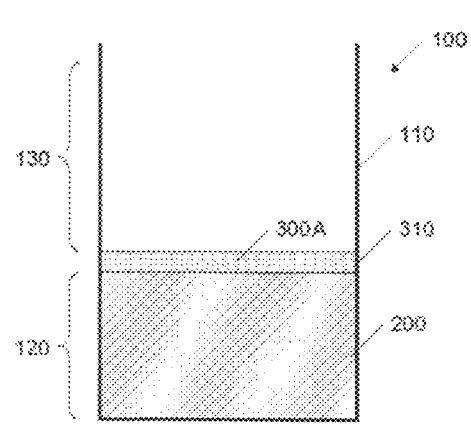
Figure 1D:
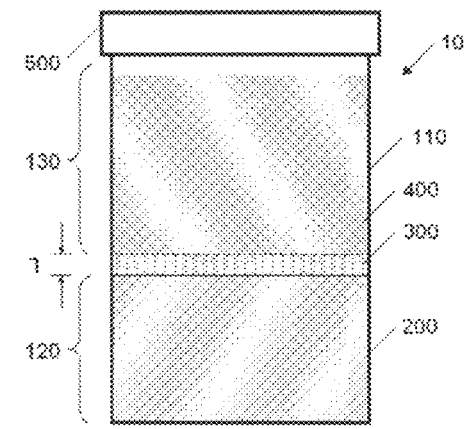
Figure 1E:
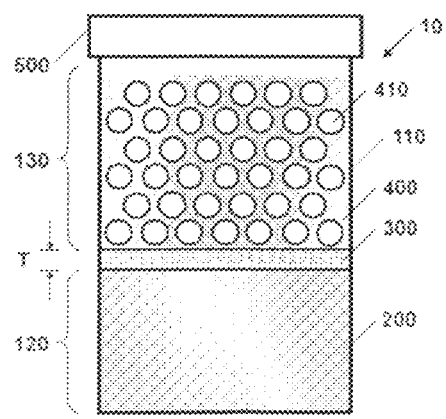

FIGS. 1A-1E illustrate an apparatus 10 for detecting a gas and a method for making the apparatus 10. The particular gas can be carbon dioxide or any other gas such as a gas metabolite of a microorganism of interest to be detected by the apparatus 10. As shown in FIG. 1D, the apparatus 10 generally includes a vessel 100 that contains a semi-permeable matrix 200, a gas-permeable membrane 300, and (optionally) a culture medium 400 (e.g., additionally containing a support material 410 for microorganism growth distributed therein as shown in FIG. 1E). The apparatus 10 can include a cap 500 or other sealing means to seal the apparatus 10 either during storage or after sample insertion into the apparatus 10 (e.g., into the culture medium 400). A general method for making the apparatus 10 includes providing the vessel 100 (FIG. 1A), for example a vessel 100 already containing the semi-permeable matrix 200 (FIG. 1B), applying the gas-permeable membrane 300 over the semi-permeable matrix 200 (FIG. 1C), (optionally) adding the culture medium 400 along with any support material 410 to the vessel 100 over the gas-permeable membrane 300, and (optionally) sealing the vessel 100 with the cap 500. The method can be performed either in a continuous process or batch process.

Vessel

The vessel 100 can have any desired shape or size, but suitably can be a vial or a tube with a circular cross-section to facilitate sealing of the apparatus 10 with the cap 500 (e.g., once a sample for analysis has been added to the culture medium 400). The vessel 100 more generally includes a wall 110 (e.g., the outer circumferential surface of a vial/tube) that defines (i) a detection region 120 in the vessel 100 and (ii) a growth region 130 in the vessel 100. As illustrated, the vessel wall 110 further defines an opening at the top of the vessel 100 to allow insertion of apparatus 10 components during manufacturing and insertion of a sample for analysis. While the detection and growth regions 120, 130 can be selected to occupy any desired interior portions of the volume defined by the vessel wall 110, the detection region 120 suitably occupies the bottom portion of the vessel 100 (i.e., the portion bounded by the wall 100 at the base of the vessel) and the growth region suitably occupies the top portion of the vessel 100 (i.e., the portion adjacent the external environment when the cap 500 is not affixed). The wall 110 of the vessel 100 is at least partially transparent in the detection region 120 to permit the detection of changes in optical properties of the semi-permeable matrix 200 during sample analysis. In an embodiment, the entire vessel wall 110 can be transparent. In another embodiment, only the vessel wall 110 in the detection region is transparent. The vessel 100 can be formed from any suitable material having the desired transparency properties, for example, glass or a transparent plastic (e.g., polystyrene, polycarbonate).

Figure 2A:
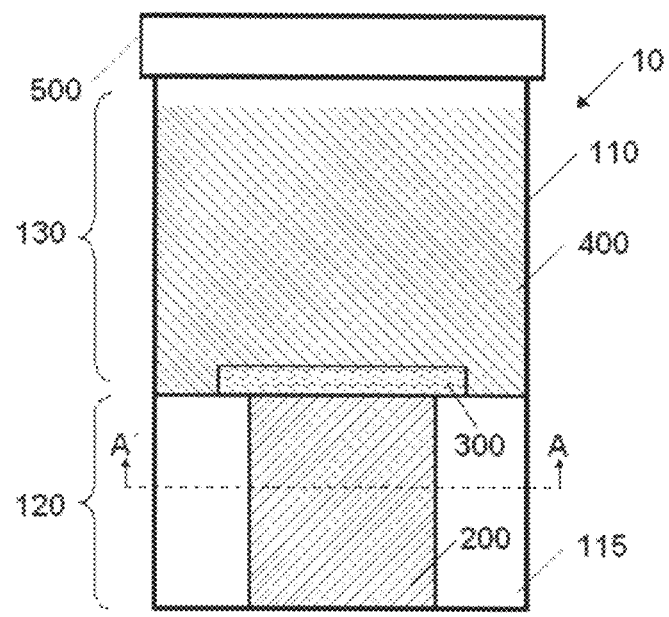
FIGS. 2A-2B illustrate an additional embodiment of a detection apparatus according to the disclosure.
Figure 2B:
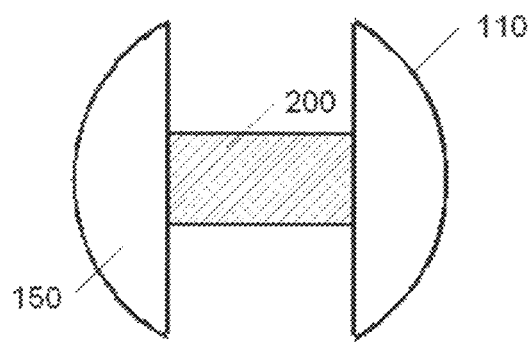

FIGS. 2A and 2B illustrate an alternate geometric configuration of the vessel 100. In FIG. 2A, the growth region 130 of the vessel 100 has a substantially circular cross-section as illustrated in FIGS. 1A-1E. However, the portion of detection region 120 that contains the semi-permeable matrix 200 has a substantially reduced cross-sectional area. As illustrated, the semi-permeable matrix 200 is contained in a rectangular channel, although other shapes are possible (e.g., a reduced-diameter cylinder relative to the major diameter of the vessel 100). The relative reduction in the size of the semi-permeable matrix 200 provides a shorter optical pathway for light passing through the detection region 120/matrix 200 and increases the relative volumetric ratio between the culture medium 400 and the matrix 200. Suitably, the optical pathway (e.g., shortest optical path for external light passing through the detection region 120/ matrix 200 such as external light normally incident thereto) is at least 0.1 cm, 0.2 cm, or 0.4 cm and/or up to 0.6 cm, 0.8 cm, 1 cm, or 2 cm. Similarly, the volumetric ratio between the growth region 130 or culture medium 400 and the detection region 120 or matrix 200 can be at least 1, 2, 5, 10, or 20 and/or up to 25, 50, or 100. Solid, semi-cylindrical sections 115, 150 of the vessel 100 that are adjacent the semi-permeable matrix 200 provide the vessel 100 with a substantially cylindrical overall shape that facilitates the handling of the vessel 100 in a manner similar to other vials. As illustrated in FIG. 2A, the gas-permeable membrane 300 is sufficiently large (e.g., in radial/lateral extent) to provide a boundary between the semi-permeable matrix 200 and the culture medium 400 and need not extend across the entire cross-section of the vessel 100 as shown in FIGS. 1C-1E; however, the membrane 300 can extend across the entire cross-section of the vessel 100 and can adhere to or otherwise contact the outer wall 110 if desired.

Semi-Permeable Matrix

As illustrated, the semi-permeable matrix 200 occupies the detection region 120 of the vessel 100. The matrix 200 includes an indicator (e.g., a single indicator or a mixture of one or more indicators, such as pH or other gas indicators) distributed (e.g., evenly or homogeneously distributed) throughout the matrix 200 (e.g., dispersed in the matrix, not reacted or otherwise bound to a substrate or other solid material either in the matrix or adjacent to/in contact with the matrix). Both the gas-permeable membrane 300 (as described in more detail below) and the semi-permeable matrix 200 are permeable to the gas of interest to be analyzed (e.g., carbon dioxide) by the apparatus 10. Such permeability permits the diffusive transport of any of the target gas analyte present in the growth region 130 to the detection region 120 during sample analysis. The semi-permeable matrix 200 additionally can be permeable to liquids, but the presence of the gas-permeable membrane 300 prevents the passage of liquids from the growth region 130 to the detection region 120 of the vessel 100.

The material forming the semi-permeable matrix 200 can be in any form such as a solid, semi-solid, or gel that has the desired gas permeability characteristics for the target gas. Suitably, the semi-permeable matrix 200 is in the form of a gel (e.g., aqueous-based gel) that includes a gelling agent such as agar, gelatin, carageenan, and/or pectin. As illustrated, the semi-permeable matrix 200 suitably is adhered to the wall 110 of (or otherwise fixed in place in) the vessel 100, for example filling a bottom portion of the vessel 100.

The semi-permeable matrix 200 suitably can be formed in the vessel 100 by first providing a mixture including (i) a liquid medium (e.g., water), (ii) a matrix-forming agent (e.g., agar, gelatin, carageenan, pectin as above) in the liquid medium, and (iii) a pH or other gas indicator in the liquid medium. The mixture is initially at a temperature sufficient to maintain the mixture in liquid form (e.g., heated to a temperature above room temperature), for example a temperature sufficient to maintain a homogeneous blend of the mixture components or a temperature sufficient to maintain the mixture as a solution in which the matrix-forming agent and the pH indicator are dissolved in the liquid medium. Suitable temperatures for particular gelling agents and/or indicators are known in the art. When in liquid form, the pH of the mixture suitably is adjusted so that the pH of the eventual matrix 200 is greater than the characteristic color-change pH of the indicator system. In such a case, the production and diffusion of carbon dioxide (or other metabolite that reduces the pH of the matrix 200) from the growth region 130 into the matrix 200 will cause a detectable color change. The heated mixture is then dispensed in liquid form into the detection region 120 of the vessel 100 by any suitable means (e.g., pouring, pipetting, metering of controlled volumes with a pump). Once dispensed, the mixture is cooled (e.g., at room temperature) for a time sufficient to allow the matrix-forming agent to solidify or otherwise assume a non-fluid state, thereby forming the semi-permeable matrix 200 with the pH indicator distributed (e.g., homogenously) throughout the matrix 200. This process is shown in FIG. 1B with the application of the matrix-forming mixture in liquid form 200A that eventually cools to form the solidified semi-permeable matrix 200. The pH of the heated mixture in liquid form is generally selected to have a value substantially above the characteristic color-change pH value for the given indicator system (e.g., 1 to 3 pH units above the color-change pH value). Once cooled to form the solid matrix 200, the matrix 200 can absorb ambient $CO_2$ (e.g., about 0.039% in air) to gradually approach an equilibrium level of $CO_2$ in the matrix 200. The absorption of ambient $CO_2$ can be from direct exposure to the atmosphere, indirect exposure to the atmosphere or to the culture medium 400 through the gas-permeable membrane 300, and/or indirect exposure to the atmosphere through the vessel wall 110. This equilibration process can require about 24 hr to 72 hr before an equilibrium or near-equilibrium level of $CO_2$ is obtained in the matrix 200 (e.g., a level of $CO_2$ close enough to equilibrium such that any further ambient $CO_2$ absorption does not substantially affect the pH (e.g., not more than +/−0.1, 0.05, 0.02, 0.01, 0.005, 0.002, or 0.001 pH units) and/or visible color of the matrix 200). In a typical process, the matrix 200, the membrane 300, and the medium 400 are solidified/cured/poured into the vessel 100 in a relatively short time (e.g., less than about 30 minutes), so the bulk of the equilibration process results from gradual $CO_2$ diffusion through the vessel wall 110 (e.g., for slightly $CO_2$-permeable plastic materials such as polystyrene) once the apparatus 10 is completely formed. As $CO_2$ is absorbed during equilibration, the pH of the matrix 200 decreases. Desirably, the initial pH of the heated, liquid matrix solution is selected to account for the $CO_2$ absorption and pH reduction such that the final, equilibrated pH value of the matrix 200 is above, but close to, the characteristic color-change pH value for the given indicator system (e.g., within about 0.1, 0.2, 0.3, or 0.5 pH units above the color-change pH value). This selection of the final pH of the matrix 200 permits relatively fast response to relatively low levels of bacteria in the culture medium 400, as a relatively lower amount of $CO_2$ is required to be metabolized and transported to the matrix 200 to generate a detectable color change. Conversely, pH values of the matrix 200 that are substantially above the color-change value can result in an apparatus 10 that responds relatively slowly (or not at all) to microorganism growth. Alternatively or additionally, the selection of the final pH of the matrix 200 can correspond to a ratio of monitoring absorbance wavelengths (as described in more detail below) approximately equal to unity.

A variety of different indicators can be used as the active molecular species in semi-permeable matrix 200. Many indicators that are responsive to the presence of a gas to provide an optical signal (e.g., a color change in the visible spectrum) are known in the art. Suitably, the indicators are responsive to gases that are representative of metabolic products released as a result of microorganism growth (e.g., carbon dioxide most notably, potentially also including others such as oxygen, nitrogen, and/or hydrogen). The mechanism of the interaction between the indicator and the gas that generates the optical signal is not particularly limited. However, the gas indicator is suitably a pH indicator that produces an optical signal/color change based on a change in pH that is induced by the presence of the target gas of interest in the semi-permeable matrix 200 (e.g., in combination with other components thereof). For example, the diffusion of carbon dioxide into a semi-permeable water-based agar matrix induces a pH change in the matrix that can be detected by any of a variety of pH indicators. The pH indicator suitably has an acceptable dynamic pH range that is readily detectable by existing optical detection technologies. For example, the pH indicator can exhibit a color change at a pH value ranging from 6 to 10, 6 to 8, 6.5 to 7.5, or 6.8 to 7.2. Examples of suitable pH indicators include those in xanthene, phenolphthalein, and phenolsulfonphthalein groups, such as bromothymol blue, xylenol blue, methyl orange, α-naphtholphthalein, fluorescein, coumarin, phenolphthalein, thymolphthalein, thymol blue, xylenol blue, α-naphtholbenzein, and combinations/mixtures thereof. The particular amount of a given pH indicator included in the semi-permeable matrix 200 can be selected based on a desired intensity of the induced color change, but suitable amounts generally can range from 0.00001 wt. % to 0.1 wt. % (e.g., 0.001 wt. % to 0.01 wt. %) based on the weight of the matrix 200. The pH or gas indicator need not be incorporated into the gas-permeable membrane 300 and/or the culture medium; in an embodiment, the gas-permeable membrane 300, the growth region 130 of the vessel 100, and/or the culture medium 400 are free or substantially free (e.g., at a level too low for visual or other optical detection of a color change, free of any indicator intentionally added to the culture medium, gas-permeable membrane, or their respective precursor components) of any pH, gas, or other indicators present in the semi-permeable matrix 200.

In an embodiment, the pH indicator represents a combination of two or more pH indicators (e.g., reactive to produce a color change at different pH values), for example a first indicator and a second indicator. In such an embodiment, the semi-permeable matrix 200 has a selected pH value (e.g., initial pH value at time of manufacture and prior to sample analysis) and includes the first indicator and the second indicator in amounts such that (i) the semi-permeable matrix 200 has a first optical absorbance at a first wavelength (e.g., in the visible spectrum, such as 615 nm), (ii) the semi-permeable matrix 200 has a second optical absorbance at a second wavelength (e.g., a different wavelength in the visible spectrum, such as 420 nm), and (iii) a ratio of the first absorbance to the second absorbance ranges from 0.2 to 4, 0.5 to 1.5, or 0.8 to 1.2. Other suitable values for the ratio include at least 0.2, 0.3, 0.5, or 0.8 and/or up to 1, 1.2, 1.5, 2, 3, or 4. The values and/or ranges of the ratio can represent an initial relative absorbance ratio (e.g., in the apparatus 10 as manufactured and after a sufficient $CO_2$ equilibration period, prior to any sample introduction/analysis in the apparatus 10) and/or a range of relative absorbance ratios in the matrix 200 experienced as $CO_2$ is absorbed during sample analysis to reduce the pH of the matrix 200 and, correspondingly, to reduce the relative absorbance ratio. A initial relative absorbance ratio that is close to 1 improves both the detection speed and the dynamic range of gas concentrations that can be detected with the apparatus 10. More than two indicators can be included in the matrix 200, and selected pairs of indicators can similarly have the indicated relative absorbance values. In an embodiment, the pH indicator is a combination of bromothymol blue (e.g., at 0.001 wt. % to 0.1 wt. %) and xylenol blue (e.g., at 0.0001 wt. % to 0.01 wt. %).

Gas-Permeable Membrane

The gas-permeable membrane 300 is located inside the vessel 100 (and defines a boundary 310 between the detection region 120 and the growth region 130 of the vessel 100. The gas-permeable membrane 300 is impermeable to liquid and solid materials present in the growth region 130, thus preventing the contamination of the semi-permeable matrix 200 with any liquids (e.g., the culture medium 400 or liquid material from a sample to be tested) or solids (e.g., solid material from a sample to be tested) that could otherwise interfere with the optical detection of a color change in the matrix 200. The gas-permeable membrane 300 is generally non-porous (e.g., free from pores, such as those sized to permit passage of liquids and/or solids therethrough). Thus, the gas-permeable membrane 300 generally permits transport and (given sufficient time) equilibration of at least some gaseous species (in particular $CO_2$) between the culture medium 400 and the semi-permeable matrix 200. Conversely, the gas-permeable membrane 300 generally prohibits transport and equilibration of liquid and solid (e.g., dissolved or suspended) species between the culture medium 400 and the semi-permeable matrix 200. In an embodiment, the gas-permeable membrane 300 can span the entire cross-section of the of the vessel 100 (e.g., as in FIGS. 1D and 1E) and optionally can be adhered the vessel wall 110 to form a barrier isolating the detection region 120 from the growth region 130 (e.g., adhered due to the use of an adhesive or due to the natural interaction of the membrane 300 and vessel wall 110 materials). In another embodiment, the gas-permeable membrane 300 span a sufficient portion of the cross-section of the vessel 100 (e.g., as in FIG. 2A) so that it still provides the boundary 310 between the detection region 120 and the growth region 130 of the vessel 100, but need not necessarily be in contact with the outer wall 110 of the vessel.

The gas-permeable membrane 300 desirably has a thickness T that is sufficiently large to provide structural integrity to the barrier it forms between the detection and growth regions 120, 130. In particular the membrane 300 desirably has sufficient structural integrity so that it does not rupture, become detached from the vessel wall 110, or otherwise become compromised to the point of allowing liquid and solid materials from the growth region 130 to contaminate the matrix 200. As a competing consideration, the membrane 300 desirably has a thickness T that is relatively smaller to enhance the diffusive transport of the target gas analyte across the membrane from the growth region 130 to the detection region 120. Depending on the particular material used for the gas-permeable membrane 300, the membrane suitably has a thickness ranging from 10 μm to 2000 μm (e.g., 10 μm to 1000 μm, 20 μm to 500 μm, 50 μm to 200 μm, 10 μm to 100 μm, 10 μm to 50 μm, 20 μm to 50 μm, at least 10 μm, 100 μm, 200 μm, or 500 μm, up to 1000 μm, 1500 μm, or 2000 μm). Similarly depending on the material used, the membrane 300 suitably has a permeability sufficient to permit timely detection of a target analyte (e.g., less than 5 hr, 10 hr, 20 hr, 50 hr, 100 hr and/or at least 1 min, 30 min, 1 hr, 2 hr, 4 hr), for example a permeability ranging from $1\times10^{-12}$ $cm^2/(sec \cdot Pa)$ to $1\times10^{-8}$ $cm^2/(sec \cdot Pa)$ or $1\times10^{-11}$ $cm^2/(sec \cdot Pa)$ to $1\times10^{-9}$ $cm^2/(sec \cdot Pa)$ for the target gas analyte (e.g., carbon dioxide).

The gas-permeable membrane 300 can generally include any of a variety of known materials having the ability to selectively permit the diffusion of the target analyte gas therethrough while being relatively impermeable to liquids in general. In particular, the membrane 300 desirably has a good permeability of gases including such as carbon dioxide and a good resistance to water penetration. Examples of suitable materials for the membrane 300 include various polymeric materials having the desired permeability characteristics such as silicone polymers (e.g., polysiloxanes), latex rubbers, polytetrafluoroethylenes, low density polyethylenes, polystyrenes, and polyacrylates. Crosslinked/vulcanized silicones (e.g., $[R^1R^2SiO]_n$ where $R^1$ and $R^2$ variously can be organic groups such as methyl and/or crosslinking groups) are particularly suitable and can be formed from any of variety of functionalized silicone monomers (e.g., for example, dimethyldichlorosilane, dimethyldiacetoxysilane, dimethylsilanediol, dimethylsilane, dimethylbis(s-butylamino)silane, and 1,3-divinyltetraethoxydisiloxane), crosslinking agents, crosslinking catalysts, and/or polysiloxane precursors (e.g., functionalized polydimethylsiloxane such as H-functionalized or vinyl-functionalized PDMS), for example including room-temperature-vulcanized silicones, high-temperature-vulcanized silicones, ultraviolet-vulcanized silicones, and/or catalytically-vulcanized silicones. A particularly suitable two-component, UV-cure silicone with liquid precursors (including a functionalized methoxysilane crosslinking agent and a hydrogen-functionalized polydimethylsiloxane) containing a photoinitiator is commercially available as DYMAX CURE-POINT 9440-A/B (available from DYMAX Corporation, Torrington, Conn.). For membranes 300 that are formed in situ within the vessel 100 (e.g., the above silicones), by-products of the curing/crosslinking reaction can remain in the final membrane 300 and can leach into the matrix 200 and/or the culture medium 400. Accordingly, the specific membrane 300 materials are suitably selected so that curing by-products that substantially affect the desired pH equilibrium in the matrix 200 and/or the ability of microorganisms to grow in the medium 400 are reduced or avoided. Examples of by-products that can be undesirable in excess include acids (e.g., strong acids such as HCl) and bases that substantially affect the pH of the matrix 200, making it difficult to obtain a stable, repeatable pH value in the matrix 200 during the equilibration process. Additionally, acidic or basic curing by-products can be toxic to the point that microorganisms in the medium 400 cannot grow quickly enough (or at all) to enable their detection. Thus, membrane 300 materials that have pH-neutral (or only mildly acidic/basic) by-products or substantially no by-products are suitable.

In an embodiment, the gas-permeable membrane 300 is formed in the vessel 100 by liquid polymeric precursor components that can be cured (e.g., vulcanized, crosslinked, and/or otherwise reacted/polymerized) in situ to form a non-liquid reaction product that serves as the membrane 300 having the desired permeability, thickness, and structural properties. More specifically, a gas-permeable membrane precursor is applied in liquid form 300A to an exposed surface of the semi-permeable matrix 200. The volume of the precursor liquid 300A is selected and controlled (e.g., pouring, pipetting, metering of controlled volumes with a pump) so that the liquid 300A will (i) sufficiently cover the interfacial area between the semi-permeable matrix 200 and the growth region 130 and (ii) result in a membrane 300 having a desired thickness T, thereby ensuring that the resulting membrane 300 will have the desired permeability and structural boundary properties between the culture medium 400 and the matrix 200. The volume of the precursor liquid 300A also can be selected to be sufficiently large enough to extend to the vessel wall 110 as illustrated in FIG. 1C so that the eventual membrane 300 will be adhered to the wall 110. Once applied, the gas-permeable membrane precursor liquid 300A is cured to form the gas-permeable membrane 300 in the vessel 100. The particular nature of the curing depends on the nature of the precursor components, and can include the application of room-temperature heat, the application of heat above room temperature, the application of ultraviolet light, and/or the exposure to atmospheric moisture.

Liquid silicone precursors are particularly suitable for forming the gas-permeable membrane 300. The liquid silicone precursor generally includes mixture of a silicone prepolymer, a silicone crosslinking agent, and optionally a curing catalyst (e.g., which could be activated by heat, ultraviolet light, or other means). An ultraviolet-curable silicone precursor mixture can be polymerized by ultraviolet irradiation (e.g., 280 nm to 400 nm excitation) applied for a time sufficient to complete the polymerization/crosslinking reaction depending on the thickness T of the membrane 300 (e.g., about 10 to 60 seconds). The ultraviolet irradiation can be applied continuously for the entire desired time, or it can be applied in intermittent pulses alternating between short irradiation periods and short non-irradiation periods.

Culture Medium

The culture medium 400 can be any suitable medium (e.g., liquid/aqueous based) known in the art for microorganism growth promotion and/or for microorganism viability maintenance. The culture medium can be selected to promote growth and/or viability of a specific microorganism of interest or class of microorganisms of interest that generates a detectable gas metabolite such as carbon dioxide. Tryptic Soy Broth (TSB), Letheen Broth and Nutrient Broth are examples of suitable media applicable to a broad range of microorganisms of interest. The culture medium 400 can be dispensed into the growth region 130 of the vessel 100 by any suitable means (e.g., pouring, pipetting, metering of controlled volumes with a pump) at any desired time prior to sample analysis. For example, the apparatus 10 can include the culture medium 400 at the point of manufacture (i.e., when the semi-permeable matrix 200 and the gas-permeable membrane 300 are formed in the vessel 100) or the culture medium 400 can be manually added by a user just prior to sample analysis.

In some embodiments (e.g., as illustrated in FIG. 1E), the growth region 130 of the vessel 100 can additionally include a support material 410 in the culture medium 400. When included, the support material can be added to the growth region before, after, or at the same time as the culture medium 400. In an embodiment, the support material 410 may be added to the growth region in the absence of the culture medium 400 (e.g., when the culture medium 400 is intended to be added by a user at a later time). The support material 410 is not particularly limited and generally can include any solid or semi-solid material that facilitates the growth of certain microorganisms (e.g., yeast, mold) in the culture medium 400, for example by providing a substrate onto which the microorganisms can attach or otherwise grow during the sample analysis cycle. The support materials can be formed from a polymer material (e.g., rigid thermoplastic or thermoset plastics) or from other organic or inorganic materials. Suitable support morphologies similarly are not particularly limited and generally can include high surface area (e.g., high surface area-to-mass or volume ratio) and high void volume (e.g., providing ample space for the culture adjacent the support material) materials such as porous materials (e.g., a sponge or a foam) and/or packed/suspended particulate materials (e.g., beads). Particular support materials generally known in the art can include sponges (e.g., a natural cellulose sponge), foams (e.g., polymeric foams such as polydimethylsiloxane, polyurethane, polyethylene, and/or polyvinylalcohol foams), and/or beads (e.g., polymeric beads such as polyethylene and/or polyvinylalcohol beads). For example, FIG. 1E illustrates a plurality of beads 410 (e.g., polymeric beads) as the support material. The beads 410 can be packed in the growth region 130 and/or suspended in the culture medium 400 (e.g., when the beads 410 are less dense than the medium 400); in any event, the spherical shape of the beads 410 provides ample interstitial volume for the medium 400 in the growth region 130.

Sample Analysis

The apparatus 10 in any of the foregoing embodiments can be used to detect the presence of a target analyte gas (e.g., carbon dioxide) either in or generated by a sample. For example, a sample to be tested can be inserted into the culture medium 400 at a first time (e.g., initial time $t_1$), and the vessel 100 is then sealed. Once sealed, the vessel 100 can be incubated at a controlled temperature (e.g., ranging from 15° C. to 60° C. for an incubation time ranging from 4 hr to 120 hr). In any event, once sealed, the detection region 120 is monitored at a second time (subsequent time $t_2 > t_1$) to detect changes in color of the pH indicator in the semipermeable matrix 200. Suitably, the detection region 120 can be monitored while the sample is being incubated such that the time $t_2$ represents a time during the incubation period. The second time can represent one or more discrete points in time at which the color of the matrix 200 is evaluated. Alternatively or additionally, the second time can represent an essentially continuous series of points in time at which the color of the matrix 200 is evaluated (e.g., to represent a continuous, real-time monitoring process that can return as an analytical result the time at which a positive result, if any, was obtained). If a change in the color of the pH indicator in the matrix 200 is noted between the first time and the second time, such a change is correlated with the presence the target analyte gas in the detection region 120/matrix 200 (or, alternatively, in the culture medium 400). Similarly, the detected color change/presence of the target analyte gas can be further correlated with the presence of a microorganism in the sample (e.g., a particular type and/or class of microorganism, depending on the nature of the culture medium 400). Conversely, the absence of any detectable color change can be correlated with the absence of a detectable level of the target analyte gas and/or microorganism(s) of interest. A suitable apparatus capable of performing simultaneous controlled-temperature incubation and real-time optical monitoring of the detection region 120 is the SOLERIS Automated Optical System (available from Neogen Corporation, Lansing, Mich.). Other suitable commercially available UV/VIS spectrophotometers (e.g., Beckman Coulter DU Series 700 or Thermo Scientific Evolution 160) can be used to collect discrete or real-time measurements of the color change in the detection region 120. In a suitable detection apparatus, a light source is directed horizontally through the detection region 120/matrix 200 (e.g., in a direction normal to the vial wall 110 adjacent the detection region 120/matrix 200, such as from top to bottom through the matrix 200 in the view shown in FIG. 2B), and the transmitted light is detected with an optical sensor on the opposing side of the detection region 120/matrix 200. Suitably, the light source is positioned so that the optical path of the light emitted therefrom is near (e.g., about 1 mm to 3 mm away from) the membrane 300/matrix 200 interface, thus increasing the rate of detection for the diffusion-controlled transport of gases into the matrix 200.

The sample can be any type of material, and suitably represents a food, food-related, or food-industry products. Samples of solid foods or liquid foods/drinks can be added to the culture medium 400 and tested with the apparatus 10. The sample also can be used to test food processing equipment or food preparation surfaces, for example by swabbing the equipment or surface and then adding the swab (or other material to wipe/test the surface) to the culture medium 400. Other suitable sample types include consumer products (e.g., personal care products, cosmetics), nutraceutical products, environmental samples (e.g., residential, commercial, or industrial water, drinking water, waste water, soil, or other material).

The microorganisms detectable by the apparatus 10 are not particularly limited and can include bacteria (aerobic or anaerobic, for example including obligate anaerobes, facultative anaerobes, microaerophilic bacteria, and aerotolerant bacteria), yeasts, and/or molds that produce a detectable gas such as carbon dioxide as a metabolite. Non-limiting examples of detectable organisms include Enterobacteriaceae (e.g., *Escherichia coli*), *Bacillus* spp., *Staphylococcus* spp. (Coagulase-negative *Staphylococcus*, *S. aureus*), *Streptococcus* spp. (*S. pneumoniae*, Group A, Group B, Enterococci), *Micrococcus* spp., *Kocuria* spp., *Aeromonas* spp., yeast (*Candida* species (e.g., *C. albicans*), *Cryptococcus neoformans*, *Torulopsis glabrata*), nonfermentors (*Pseudomonas* spp. (e.g., *Ps. aeruginosa*), *Acinetobacter calcoaceticus*), anaerobes (*Bacteroides fragilis*, *Clostridium perfringens*, *Fusobacterium necrophorum*, *Peptostreptococcus anaerobius*), other microorganisms (*Haemophilus influenzae*, *Neisseria meningitidis*), and *Aspergillus niger* (mold).

EXAMPLES

The following examples illustrate the disclosed apparatus and related methods, but are not intended to limit the scope of any claims thereto. In the examples, bromothymol blue and xylenol blue were obtained from Sigma-Aldrich (St. Louis, Mo.), Noble Agar was obtained from Becton Dickinson and Company (Franklin Lakes, N.J.), and the UV-vulcanized silicone was obtained from Dymax Corporation (Torrington, Conn.).

Example 1—Batch Process for Making Detection Apparatus

Bromothymol blue (BB; 0.01 wt %) and xylenol blue (XB; 0.001 wt. %) were dissolved in deionized water containing 0.8 wt. % Noble Agar that was heated while stirring. While the agar indicator solution was at 45° C., the pH was adjusted to pH 8.5, and the ratio of absorbance at 615/420 nm was about 3.9. The adjustment of pH provides an improved response to changes in carbon dioxide concentration. The warm indicator solution was added to a polycarbonate container with optically transparent windows. The indicator solution was allowed to cool at room temperature and solidify in the polycarbonate, thus forming a semipermeable indicator matrix according the disclosure. The indicator matrix was then covered with a layer of polydimethylsiloxane by dispensing the liquid DYMAX CURE-POINT silicone precursor into the vial and then curing the precursor in-situ to forma silicone membrane according to the disclosure having a thickness of about 500 µm to 750 µm. During the silicone curing process and equilibration with ambient $CO_2$, the agar/indicator color stabilizes (e.g., after about 48 hours), the pH of the agar matrix becomes about 7 to 7.5, and the 615/420 nm absorbance ratio is between 0.3 and 1.0. This layer permits permeation of carbon dioxide into the indicator matrix. In some cases Tryptic Soy Broth (TSB) media was added over the semipermeable layer. The test device was then capped with a screw cap.

The foregoing process was used to form a sampling apparatus 10 as illustrated in FIGS. 2A and 2B. The apparatus 10 included a Tryptic Soy Broth culture growth media 400, a polydimethylsiloxane gas-permeable membrane 300, and an indicator solution of bromothymol blue and xylenol blue in an agar matrix 200.

The formed apparatus 10 was evaluated for the change in visual appearance of the pH indicator solution in the agar/indicator matrix 200 upon exposure to carbon dioxide. For this evaluation, there was no bacterial growth media 400 in the vial 100; only the agar/indicator 200 and the silicone membrane 300 were present. At t=0 hours, the semi-permeable pH indicator matrix 200 had a dark green color corresponding to its initial 620/415 nm absorbance ratio of 0.9 and pH of 7.2. The vial 100 was placed in a gas incubation chamber and exposed to 0.2% carbon dioxide using a feed from a $CO_2$ compressed gas cylinder, and its visible color was monitored over time. At t=24, 48, and 72 hours, the pH indicator matrix 200 had a yellowish orange color corresponding to the absorption of a sufficient amount of carbon dioxide to lower the pH below the color-change value of the pH indicator matrix 200.

The pH dependence of the color and relative absorbance values of an indicator/agar matrix including 0.01% bromothymol blue and 0.001% xylenol blue was evaluated. The data are summarized in Table 1 below and were obtained using indicator/agar deposited and solidified in a polycarbonate cuvette with the visible spectrum acquired on a UV spectrophotometer. The pH of the indicator/agar mixture was adjusted to obtain an absorbance ratio (615/420 nm) in the desirable range of 0.7 to 1.1 at pH values of 6.8 and 7.2 after $CO_2$ equilibration but prior to $CO_2$ exposure at levels higher than atmospheric levels. Rows 2 (green; pH of 6.8) and 3 (greenish blue; pH of 7.2) of Table 1 for these pH values show the colors of the indicator/agar mixture adjusted to the desired range prior to $CO_2$ exposure. The first row of the table shows the color (greenish yellow), pH and visible spectrum absorbances of the indicator/agar at a pH of 6.5 and absorbance ratio of 0.3 which is at the low end of desirable absorbance ratios because the initial color is close to the transition color detected upon exposure to $CO_2$.

TABLE 1

Color and Absorbance as a Function of pH for
0.01% Bromothymol Blue and 0.001% Xylenol Blue in Agar

| pH | Color | Absorbance | | |
|---|---|---|---|---|
| | | at 420 nm | at 615 nm | Ratio 615 nm/420 nm |
| 6.5 | Greenish Yellow | 1.9 | 0.4 | 0.3 |
| 6.8 | Green | 1.6 | 1.1 | 0.7 |
| 7.2 | Greenish Blue | 1.4 | 1.6 | 1.1 |

Figure 3:
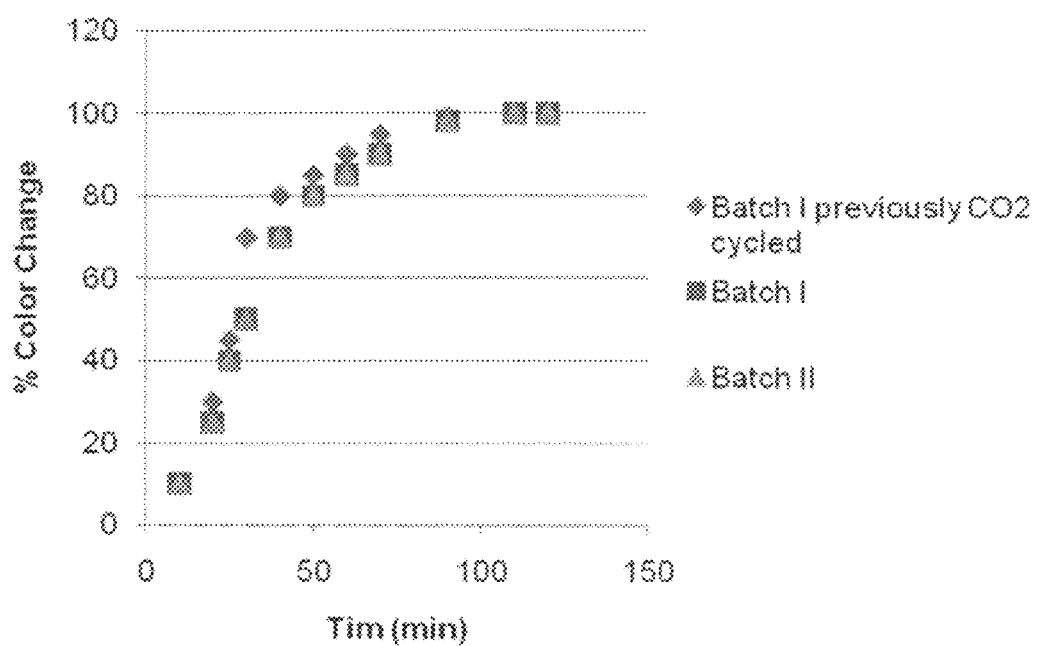
FIG. 3 illustrates the rate of change in color of the indicator solution upon exposure to carbon dioxide.

FIG. 3 illustrates the repeatability of optical measurements made with the formed detection apparatus. Two vials ("Batch I" and "Batch II") as described above and illustrated in FIGS. 2A and 2B were exposed to 3% $CO_2$ (compressed source of gas fed to an incubation chamber), and the percent color change was measured as a function of time. The percentage color change shown in FIG. 3 is the lineal distance of yellow color formation as a percentage of the total length of indicator/agar as $CO_2$ penetrated through the length of the indicator/agar plug (i.e., the relative position of the yellow-to-green transitional front that moves from the top of the agar matrix to the bottom of the matrix as a function of time). The consistency of the data for Batches I and II indicates that repeatable transient responses can be obtained from different vials in the same manufacturing batch. The vial from Batch I was then removed from the 3% $CO_2$ environment, placed in an ambient environment until the color changed back to green, and again exposed to 3% $CO_2$ to demonstrate the repeatable kinetic response of the color change in a recycled agar matrix/detection apparatus ("Batch I Cycled").

Example 2—Continuous Process for Making Detection Apparatus

The general procedure in Example 1 for making the disclosed detection apparatus can be extended to a continuous production process. Polystyrene or other suitable plastic vials are fed through a vibrating bin onto a conveyance system. The vibrating bin sorts the vials so they are oriented with their open end up and spaced evenly apart. The vials pass under a dispensing head that feeds a known amount of heated pH indicator/agar solution into the bottom of each vial. The indicator/agar solution cools and solidifies as it proceeds along the conveyor. The vials then pass under another dispensing head that feeds a known amount of liquid silicone precursor on top of the solidified semi-permeable matrix. The silicone reagent contains a mixture of monomers and a photo initiator that initiates polymerization. The vials pass under a series of UV light sources that irradiate the liquid silicone precursor to polymerize/crosslink the silicone precursor. The vials then pass under a dispensing head that feeds a known amount of bacterial/mold growth media into the vials. The vials then are automatically capped and are ready to box as a ready-to-use detection apparatus.

The pH indicator/agar solution is formed by adding 0.01 wt. bromothymol blue, 0.001 wt, % xylenol blue, and 125 µL of 4M NaOH to 0.85 wt. % Difco Noble Agar in 2.0 L of Type I water. The indicated mixture of bromothymol blue and xylenol blue is chosen to afford optimal color change of the indicator for bacterial and/or mold growth. Other sources of agar can be used, but they may require a different pH adjustment. In particular, the amount of base used is determined such that an equilibrium absorbance ratio of 615/420 nm is obtained at a desired value such as 0.7 to 1.0. When the indicator/agar is first pH-adjusted, the color is dark green/blue, the pH is about 8.8, and the absorbance ratio is substantially higher than 1.0 (about 3.9). After depositing the indicator/agar into the vial, the mixture cools to form the indicator/agar matrix, the matrix then equilibrates with ambient $CO_2$, and equilibrates with components released from the curing silicone polymerization (i.e., once the silicone membrane is formed) for about 48 hours. The final color obtained is green, the pH is about 7.2, and the equilibrium absorbance ratio of 615/420 nm is between 0.7 and 1.0. The indicator/agar solution is heated until the agar is melted/dissolved into the aqueous matrix. The indicator/agar solution is autoclaved for 15 minutes at 121° C. and 15 psi pressure. After autoclaving, the solution is cooled to about 40° C. to 45° C. and the final color/pH of the indicator/agar solution is adjusted by adding 100 mM sterile filtered sodium hydroxide solution until the pH is 8.8±0.8. The heated, pH-adjusted indicator/agar solution is transferred to a reservoir maintained at a constant temperature with a water bath to keep the solution components dissolved. The indicator/agar solution is withdrawn/metered from the reservoir in controlled amounts via insulated plastic tubing (i.e., to prevent precipitation/solidification of the agar prior to addition to the sampling vial) using a peristaltic pump dispensing unit through a dispensing head. In an embodiment, about 400 µl of the indicator/agar solution is dispensed into the detection region of a vial corresponding to that schematically illustrated in FIGS. 2A-2B. The illustrated vial has a height of about 6 cm, an outer diameter of about 2 cm, holds about 400 µL in the detection region 120, and holds about 10 mL in the growth region 130. About 30 sec is required between addition of the indicator/agar and sufficient solidification of the matrix for addition of the silicone barrier layer.

The CURE-POINT ultraviolet-curable liquid silicone precursor (about 200 µL per vial) is dispensed into the vial over the solidified indicator/agar matrix using transfer lines that pass through a peristaltic pump dispensing unit into a dispensing head. Alternatively, a pneumatic pump can be used to improve the tolerance of delivered fluid volume. The dispensing head is grounded to prevent static build-up that could alter uniformity of the silicone membrane layer.

Thickness of the polymerized silicone layer is important for optimal detection speed and protection of the indicator/agar mixture from the growth media layer. The estimated silicone membrane thickness for the 200 μL of liquid precursor was about 500 μm to 750 μm.

Minimizing capital expense while ensuring adequate silicone layer polymerization (i.e., to ensure the formation of solid gas-permeable membrane) can be controlled with the number and length (in time) of ultraviolet irradiation steps applied to each vial in the continuous production process. Patterns of consecutive irradiation and non-irradiation periods that permit adequate curing (polymerization) of the silicone reagent prior to addition of growth media are experimentally determined. A suitable pattern for the continuous production process is a series of 3-second UV irradiations and 6-second non-irradiated periods. Overall, adequate product stability and minimization of irradiation stations can be achieved using a series of 6 of the 3-second irradiation and 6-second non-irradiation periods. The vials in the continuous process are moving positions every 2-3 seconds. Optical fibers were used to deliver a concentrated beam of UV radiation. The 6 sequential irradiation/non-irradiation periods cured the silicone better than a single continuous pulse, thus improving the reliability of the product by decreasing the failure rate due to a ruptured silicone layer. Adequate silicone barrier layer stability is defined as polymerization with less than a 2% failure rate of the polymerized silicone layer to prevent penetration of the growth media layer into the pH indicator/agar matrix.

Example 3—Determination of Indicator Composition

Figure 4:
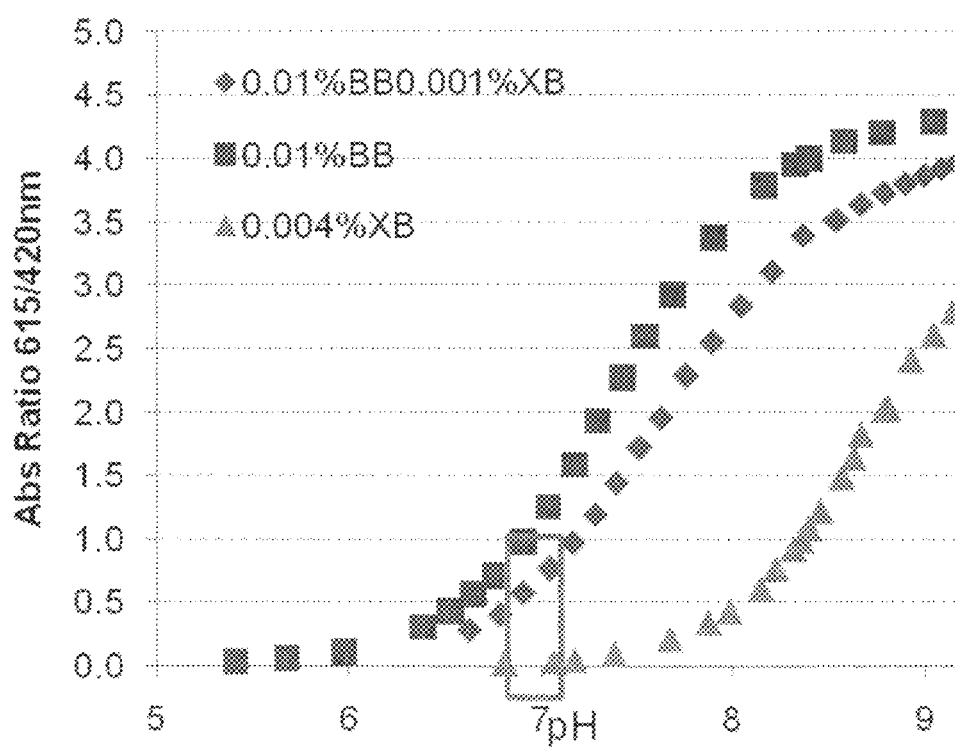
FIG. 4 illustrates the absorbance properties of pH indicators according to the disclosure as a function of indicator composition and pH.

FIG. 4 illustrates the absorbance properties (absorbance ratios at 615 nm/420 nm) of pH indicators according to the disclosure as a function of indicator composition in the gas permeable matrix: (i) 0.01 wt. % bromothymol blue and 0.001 wt, % xylenol blue (diamond), (ii) 0.01 wt. % bromothymol blue (square), and (iii) 0.004 wt, % xylenol blue (triangle). The box highlights an area of interest around pH values of 6.8 to 7.2. This is where the indicator color desirably changes from green to yellow near the pH range of the growth media (e.g., 6.8 to 7.2 for TSB). The curve for the mixture of 0.01% BB and 0.001% XB lies in the optimal range. While BB at 0.01% will also work, its optimal pH range is slightly lower than that of the growth media and the resulting detection apparatus would require slightly more carbon dioxide production (i.e., more acidity and a longer amount of time for microorganisms in the growth medium to produce the required carbon dioxide) to reach the same yellow hue as the BB/XB indicator mixture. For a total viable count (TVC) testing application, the detection apparatus desirable can detect 1 cfu per vial in an incubation time of about 24 hours (or less).

Example 4—Alternative Detection Apparatus Embodiment

Figure 5A:
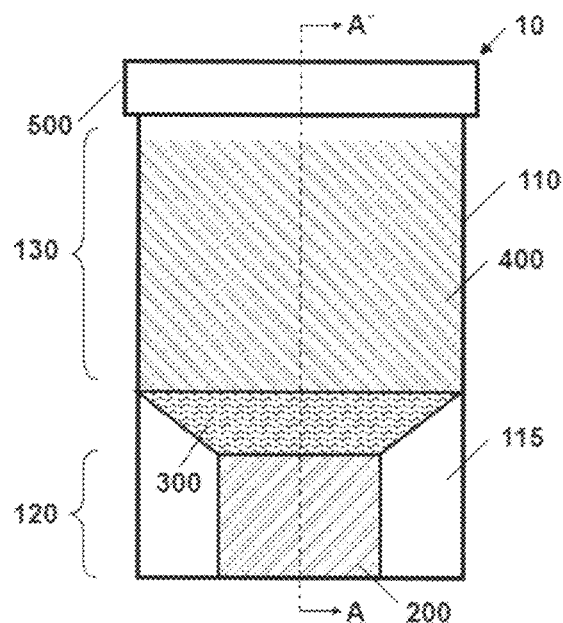
FIGS. 5A-5B illustrate an additional embodiment of a detection apparatus according to the disclosure.
Figure 5B:
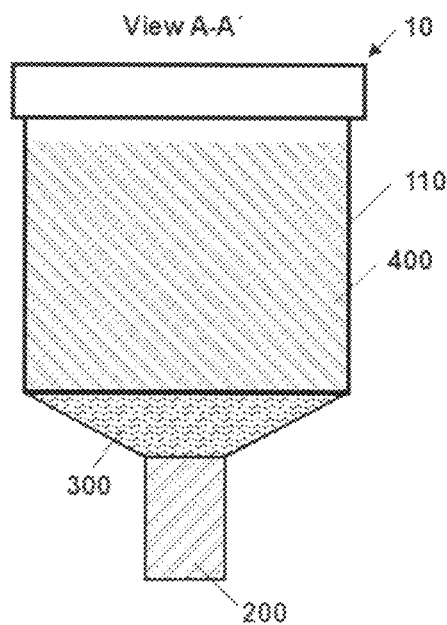

Example 4 and the accompanying FIGS. 5A and 5B illustrate an additional embodiment of the detection apparatus 10 than can be formed according to the general disclosure above and the specific methods of Example 2. FIG. 5A is a front view schematic of the device 10, and FIG. 5B is a side cross-section schematic of the device 10 along line A-A'. In relation to the devices of FIGS. 1 and 2, like numerals represent the same structural components. As shown, the agar-indicator matrix 200 occupies a rectangular optical channel with internal dimensions of about 1 cm×0.8 cm×0.5 cm (W×H×D). The vial wall 110 has a beveled, sloped transition between the cylindrical growth region 130 and the rectangular channel-shaped detection region 120. This beveled structure creates an inverted, truncated pyramid-shaped region occupied by the silicone membrane 300 (i.e., as illustrated in FIGS. 5A and 5B with an exaggerated thickness). The silicone membrane 300 has a thickness of about 1 mm at its thickest point immediately above the agar-indicator matrix 200. As shown, the membrane 300 extends beyond the exposed portion of the agar-indicator matrix 200 where it contacts or adheres to the sloped portion of the vial wall 110 to provide a sealed gas-permeable barrier between the detection region 120 and the growth region 130. The transparent polystyrene vial 100 has two semi-cylindrical sections 115 at its base to facilitate handling and stable vertical placement of the vial 100 as well as insertion of the vial 100 into an optical detection apparatus.

The detector device 10 is formed in a manufacturing process that has a total cycle time of about 3 min/vial. At the beginning of the process, 400 μl of a hot, aqueous solution of agar and indicator (e.g., agar, bromothymol blue, and xylenol blue dissolved into hot deionized water) is dispensed into the channel-shaped detection region 120. The hot, liquid agar-indicator solution cools for about 20 sec to 40 sec as the vial 110 is transported to a liquid silicone precursor dispensation unit. During this transport time, the agar-indicator solution cools to form a partially set agar-indicator matrix 200 that is sufficiently solid to support a layer of liquid above the matrix. A 200 μl aliquot of the liquid silicone precursor is then dispensed onto the agar-indicator matrix 200 and cured with UV light to form a silicone membrane 300 adhered to the vial wall and completely covering the agar-indicator matrix 200. The two-step formation of the matrix 200 and the membrane 300 can avoid unintended mixing of the components of the two structures. In particular, the at least semi-solid nature of the agar-indicator matrix prior to liquid silicone precursor dispensation avoids liquid-liquid mixing of the two components. Further, the two components are generally incompatible on a molecular level, given the hydrophilic nature of the aqueous-based matrix 200 and the hydrophobic nature of the membrane 300 (e.g., whether a silicone membrane, its precursors, or otherwise).

Subsequent process steps include dispensation of a culture medium 400 (e.g., about 9 ml) into the vial 100 above the cured silicone membrane 300, capping of the vial 100, and application of a label. The manufactured device 10 is then allowed to equilibrate for 5 days, during which time ambient $CO_2$ diffuses through the vial wall 110 and a green color is obtained for the agar-indicator matrix 200. The green color remains stable for at least about 6 to 9 months.

Because other modifications and changes varied to fit particular operating requirements and environments will be apparent to those skilled in the art, the disclosure is not considered limited to the examples chosen for purposes of illustration, and covers all changes and modifications which do not constitute departures from the true spirit and scope of this disclosure.

Accordingly, the foregoing description is given for clarity of understanding only, and no unnecessary limitations should be understood therefrom, as modifications within the scope of the disclosure may be apparent to those having ordinary skill in the art.

Throughout the specification, where the compositions, processes, or apparatus are described as including components, steps, or materials, it is contemplated that the compositions, processes, or apparatus can also comprise, consist essentially of, or consist of, any combination of the recited components or materials, unless described otherwise. Component concentrations expressed as a percent are weight-percent (% w/w), unless otherwise noted. Numerical values and ranges can represent the value/range as stated or an approximate value/range (e.g., modified by the term "about"). Combinations of components are contemplated to include homogeneous and/or heterogeneous mixtures, as would be understood by a person of ordinary skill in the art in view of the foregoing disclosure.

What is claimed is:

1. An apparatus for detecting carbon dioxide, the apparatus comprising:
   (a) a vessel comprising a wall, the wall defining (i) a detection region in the vessel and (ii) a growth region in the vessel;
   (b) a semi-permeable matrix disposed in the detection region of the vessel, the matrix comprising a pH indicator distributed throughout the matrix;
   (c) a gas-permeable membrane comprising a silicone polymer selected from the group consisting of room-temperature-vulcanized silicone, high-temperature-vulcanized silicone, ultraviolet-vulcanized silicone, and combinations thereof disposed inside the vessel, the gas-permeable membrane covering the semi-permeable matrix and defining a boundary between the detection region and the growth region of the vessel; and
   (d) optionally, a culture medium disposed in the growth region of the vessel, the culture medium being capable of supporting the growth of a microorganism; wherein:
   (i) the gas-permeable membrane and the semi-permeable matrix are permeable to carbon dioxide, thereby permitting diffusive transport of carbon dioxide present in the growth region to the detection region;
   (ii) the gas-permeable membrane is impermeable to liquid and solid materials present in the growth region;
   (iii) the gas-permeable membrane is substantially free of any pH indicators present in the semi-permeable matrix;
   (iv) the wall of the vessel is at least partially transparent in the detection region; and
   (v) the semi-permeable matrix is permeable to liquids, but the presence of the gas-permeable membrane prevents the passage of liquids from the growth region to the detection region of the vessel.

2. The apparatus of claim 1, wherein the silicone polymer comprises ultraviolet-vulcanized silicone.

3. The apparatus of claim 1, wherein the gas-permeable membrane is attached to the wall of the vessel and forms a barrier isolating the detection region from the growth region.

4. The apparatus of claim 1, wherein the gas-permeable membrane has a thickness ranging from 10 pm to 2000 pm.

5. The apparatus of claim 1, wherein the gas-permeable membrane has a permeability ranging from $1\times10^{-11}$ cm$^2$/(sec·Pa) to $1\times10^{-9}$ cm$^2$/(sec·Pa) for carbon dioxide.

6. The apparatus of claim 1, wherein the semi-permeable matrix is in the form of a semi-solid or gel.

7. The apparatus of claim 1, wherein the semi-permeable matrix is in the form of a gel and comprises a gelling agent selected from the group consisting of agar, gelatin, carageenan, pectin, and combinations thereof.

8. The apparatus of claim 1, wherein the semi-permeable matrix is adhered to the wall of the vessel.

9. The apparatus of claim 1, wherein the pH indicator is evenly distributed throughout the semi-permeable matrix.

10. The apparatus of claim 1, wherein:
    (i) the pH indicator comprises a first indicator and a second indicator; and
    (ii) semi-permeable matrix comprises the first indicator and the second indicator in amounts and at a pH such that (A) the semi-permeable matrix has a first absorbance at a first wavelength, (B) the semi-permeable matrix has a second absorbance at a second wavelength, and (C) a ratio of the first absorbance to the second absorbance ranges from 0.2 to 4.

11. The apparatus of claim 1, wherein the pH indicator exhibits a color change at a pH value ranging from 6 to 10.

12. The apparatus of claim 1, wherein the pH indicator is selected from the group consisting of bromothymol blue, xylenol blue, methyl orange, α-naphtholphthalein, fluorescein, coumarin, phenolphthalein, thymolphthalein, thymol blue, xylenol blue, and α-naphtholbenzein, and combinations thereof.

13. The apparatus of claim 1, wherein the gas-permeable membrane, the growth region of the vessel, and the culture medium, when present, are free of any pH indicators present in the semi-permeable matrix.

14. The apparatus of claim 1, wherein:
    (i) the pH indicator comprises bromothymol blue and xylenol blue; and
    (ii) semi-permeable matrix comprises the bromothymol blue and the xylenol blue in amounts and at a pH such that (A) the semi-permeable matrix has a first absorbance at a first wavelength of about 615 nm, (B) the semi-permeable matrix has a second absorbance at a second wavelength of about 420 nm, and (C) a ratio of the first absorbance to the second absorbance ranges from 0.8 to 2.

15. The apparatus of claim 1, wherein the culture medium is present in the growth region of the vessel.

16. The apparatus of claim 15, wherein the culture medium comprises a Tryptic Soy Broth mixture.

17. The apparatus of claim 1, further comprising:
    (e) a support material disposed in the growth region of the vessel, the support material providing a growth substrate for the microorganism.

18. A method of making an apparatus for detecting carbon dioxide, the method comprising:
    (a) providing a vessel comprising a wall, the wall defining (i) a detection region in the vessel and (ii) a growth region in the vessel, wherein the detection region of the vessel contains a semi-permeable matrix disposed in the detection region of the vessel, the matrix comprising a pH indicator distributed throughout the matrix;
    (b) applying a gas-permeable membrane precursor comprising a mixture comprising (i) a silicone prepolymer, (ii) a silicone crosslinking agent, and (iii) a curing catalyst in liquid form to an exposed surface of the semi-permeable matrix; and
    (c) curing the gas-permeable membrane precursor, thereby forming a gas-permeable membrane in the vessel, the gas-permeable membrane covering the semi-permeable matrix and defining an interface between the detection region and the growth region of the vessel;
wherein:
    (i) the gas-permeable membrane and the semi-permeable matrix are permeable to carbon dioxide, thereby permitting diffusive transport of carbon dioxide present in the growth region to the detection region;
    (ii) the gas-permeable membrane is impermeable to liquid and solid materials present in the growth region;

(iii) the wall of the vessel is at least partially transparent in the detection region; and (iv) the semi-permeable matrix is permeable to liquids, but the presence of the gas-permeable membrane prevents the passage of liquids from the growth region to the detection region of the vessel.

19. The method of claim 18, wherein the semi-permeable matrix in part (a) is formed by a process comprising:

(i) providing a mixture comprising (A) a liquid medium, (B) a matrix-forming agent in the liquid medium, and (C) a pH indicator in the liquid medium, wherein the mixture is at a temperature sufficient to maintain the mixture in liquid form;

(ii) dispensing the mixture in liquid form into the detection region;

(iii) cooling the mixture for a time sufficient to allow the matrix-forming agent to solidify, thereby forming the semi-permeable matrix comprising the pH indicator distributed throughout the matrix.

20. The method of claim 19, wherein the mixture is a solution in which the matrix-forming agent and the pH indicator are dissolved in the liquid medium.

21. The method of claim 19, wherein the matrix-forming agent is selected from the group consisting of agar, gelatin, carageenan, pectin, and combinations thereof.

22. The method of claim 18, further comprising:

(d) dispensing a culture medium in liquid form into the growth region of the vessel, the culture medium being in contact with the gas-permeable membrane and being capable of supporting the growth of a microorganism;

(e) sealing the vessel; and (f) optionally exposing the sealed vessel to an ambient source of environmental carbon dioxide for a time sufficient for the semi-permeable matrix to attain an equilibrium level of carbon dioxide.

23. The method of claim 22, wherein part (d) further comprises inserting a support material into the growth region of the vessel, the support material being in contact with the culture medium and providing a growth substrate for the microorganism.

24. The method of claim 18, comprising applying the gas-permeable membrane precursor in an amount sufficient to completely coat the exposed surface of the semi-permeable matrix and to contact the wall of the vessel.

25. The method of claim 24, wherein the semi-permeable matrix is adhered to the wall of the vessel.

26. The method of claim 18, wherein curing the gas-permeable membrane precursor comprises exposing the gas-permeable membrane precursor to ultraviolet light.

27. The method of claim 18, comprising performing parts (a)-(c) in a continuous process.

28. The method of claim 18, comprising performing parts (a)-(c) in a batch process.

29. A method of detecting carbon dioxide, comprising:

(a) providing an apparatus including (A) a vessel comprising a wall, the wall defining (i) a detection region in the vessel and (ii) a growth region in the vessel; (B) a semi-permeable matrix disposed in the detection region of the vessel, the matrix comprising a pH indicator distributed throughout the matrix; (C) a gas-permeable membrane comprising a silicone polymer selected from the group consisting of room-temperature-vulcanized silicone, high-temperature-vulcanized silicone, ultraviolet-vulcanized silicone, and combinations thereof disposed inside the vessel, the gas-permeable membrane covering the semi-permeable matrix and defining a boundary between the detection region and the growth region of the vessel: and (D) optionally, a culture medium disposed in the growth region of the vessel, the culture medium being capable of supporting the growth of a microorganism; wherein: (1) the gas-permeable membrane and the semi-permeable matrix are permeable to carbon dioxide, thereby permitting diffusive transport of carbon dioxide present in the growth region to the detection region: (ii) the gas-permeable membrane is impermeable to liquid and solid materials present in the growth region; (iii) the gas-permeable membrane is substantially free of any pH indicators present in the semi-permeable matrix; (iv) the wall of the vessel is at least partially transparent in the detection region; and (v) the semi-permeable matrix is permeable to liquids, but the presence of the gas-permeable membrane prevents the passage of liquids from the growth region to the detection region of the vessel:

wherein the culture medium is present in the growth region of the vessel;

(b) inserting a sample to be tested into the culture medium at a first time ($t_1$);

(c) sealing the vessel with the inserted sample;

(d) monitoring the detection region at a second time ($t_2 > t_1$) to detect changes in color of the pH indicator in the semi-permeable matrix; and (e) correlating a change in the color of the pH indicator between the first time and the second time with a presence of carbon dioxide in the detection region.

30. The method of claim 29, further comprising:

(f) correlating a change in the color of the pH indicator between the first time and the second time with a presence of microorganisms in the sample.

31. The method of claim 30, wherein the microorganisms are selected from the group consisting of bacteria, yeasts, molds, and combinations thereof.

32. The method of claim 30, wherein the microorganisms comprise aerobic bacteria producing carbon dioxide as a metabolite.

33. The method of claim 29, wherein monitoring the detection region comprises incubating the vessel at a controlled temperature between the first time and the second time.

34. The method of claim 29, wherein monitoring the detection region comprises visually inspecting the semi-permeable matrix in the detection region to detect the changes in color of the pH indicator.

35. The method of claim 29, wherein monitoring the detection region comprises performing a spectrophotometric detection at one or more wavelengths.

36. The method of claim 35, wherein the one or more wavelengths are in the visible spectrum.

37. An apparatus for detecting a metabolic product gas of a microorganism, the apparatus comprising:

(a) a vessel comprising a wall, the wall defining (i) a detection region in the vessel and (ii) a growth region in the vessel;

(b) a semi-permeable matrix disposed in the detection region of the vessel, the matrix comprising a gas indicator distributed throughout the matrix;

(c) a gas-permeable membrane comprising a silicone polymer selected from the group consisting of room-temperature-vulcanized silicone, high-temperature-vulcanized silicone, ultraviolet-vulcanized silicone, and combinations thereof disposed inside the vessel, the gas-permeable membrane covering the semi-permeable matrix and defining a boundary between the detection region and the growth region of the vessel; and (d) optionally, a culture medium disposed in the growth region of the vessel, the culture medium being capable of supporting the growth of a microorganism; wherein:

(i) the gas-permeable membrane and the semi-permeable matrix are permeable to a metabolic product gas of microorganism growth, thereby permitting diffusive transport of the gas present in the growth region to the detection region;

(ii) the gas-permeable membrane is impermeable to liquid and solid materials present in the growth region;

(iii) the wall of the vessel is at least partially transparent in the detection region; and (iv) the semi-permeable matrix is permeable to liquids, but the presence of the gas-permeable membrane prevents the passage of liquids from the growth region to the detection region of the vessel.

38. A method of detecting a metabolic product gas of a microorganism, comprising:

(a) providing an apparatus (A) a vessel comprising a wall, the wall defining (i) a detection region in the vessel and (ii) a growth region in the vessel; (B) a semi-permeable matrix disposed in the detection region of the vessel, the matrix comprising a gas indicator distributed throughout the matrix; (C) a gas-permeable membrane comprising a silicone polymer selected from the group consisting of room-temperature-vulcanized silicone, high-temperature-vulcanized silicone, ultraviolet-vulcanized silicone, and combinations thereof disposed inside the vessel, the gas-permeable membrane covering the semi-permeable matrix and defining a boundary between the detection region and the growth region of the vessel; and (D) optionally, a culture medium disposed in the growth region of the vessel, the culture medium being capable of supporting the growth of a microorganism; wherein: (i) the gas-permeable membrane and the semi-permeable matrix are permeable to a metabolic product gas of microorganism growth, thereby permitting diffusive transport of the gas present in the growth region to the detection region; (ii) the gas-permeable membrane is impermeable to liquid and solid materials present in the growth region; (iii) the wall of the vessel is at least partially transparent in the detection region; and (iv) the semi-permeable matrix is permeable to liquids, but the presence of the gas-permeable membrane prevents the passage of liquids from the growth region to the detection region of the vessel;

(b) inserting a sample to be tested into the culture medium at a first time ($t_1$);

(c) sealing the vessel with the inserted sample;

(d) monitoring the detection region at a second time ($t_2 > t_1$) to detect changes in color of the gas indicator in the semi-permeable matrix; and (e) correlating a change in the color of the gas indicator between the first time and the second time with a presence of a metabolic product gas of microorganism growth in the detection region.

* * * * *